United States Patent
Brusaca et al.

(10) Patent No.: US 12,364,456 B2
(45) Date of Patent: Jul. 22, 2025

(54) AIR FILLED CHAMBER IN AN ULTRASOUND PROBE

(71) Applicant: GE Precision Healthcare LLC, Wauwatosa, WI (US)

(72) Inventors: Marco Brusaca, Attersee am Attersee (AT); Wolfgang Neuwirth, Attersee am Attersee (AT); Christian Heinrich, Neukirchen an der Vöckla (AT); Reinhold Bruestle, Frankenburg am Hausruck (AT)

(73) Assignee: GE Precision Healthcare LLC, Waukesha, WI (US)

( * ) Notice: Subject to any disclaimer, the term of this patent is extended or adjusted under 35 U.S.C. 154(b) by 74 days.

(21) Appl. No.: 16/720,199

(22) Filed: Dec. 19, 2019

(65) Prior Publication Data

US 2021/0186462 A1 Jun. 24, 2021

(51) Int. Cl.
*A61B 8/00* (2006.01)
*B06B 1/06* (2006.01)

(52) U.S. Cl.
CPC .......... *A61B 8/4461* (2013.01); *A61B 8/4494* (2013.01); *B06B 1/0629* (2013.01); *B06B 2201/76* (2013.01)

(58) Field of Classification Search
CPC ... A61B 8/4461; A61B 8/4494; A61B 8/4455; A61B 8/4444; A61B 8/54; A61B 8/42; A61B 8/4483; A61B 2562/168; B06B 1/0629; B06B 2201/76; G01N 29/24
See application file for complete search history.

(56) References Cited

U.S. PATENT DOCUMENTS

| 5,603,327 A * | 2/1997 | Eberle | A61B 8/06 29/25.35 |
| 8,945,013 B2 * | 2/2015 | Oakley | G10K 11/355 600/459 |
| 2003/0014003 A1 * | 1/2003 | Gertner | A61M 1/3653 604/5.01 |
| 2004/0102769 A1 * | 5/2004 | Schwartz | A61N 7/022 606/27 |
| 2005/0154312 A1 * | 7/2005 | Bruestle | A61B 8/14 600/459 |

(Continued)

FOREIGN PATENT DOCUMENTS

| KR | 20160068183 A | 6/2016 | |
| WO | WO-2015166081 A1 * | 11/2015 | ............. A61L 29/14 |

OTHER PUBLICATIONS

Hedrick, James L., et al. "High-temperature polyimide nanofoams for microelectronic applications." Reactive and Functional Polymers 30.1-3 (1996): 43-53. (Year: 1996).*

(Continued)

*Primary Examiner* — Hien N Nguyen
(74) *Attorney, Agent, or Firm* — McAndrews, Held & Malloy, Ltd.; Daniel Bissing (57) ABSTRACT

An ultrasound probe comprises an air chamber unit that includes a transducer slot, where the transducer slot is configured to receive a transducer assembly, the air chamber unit comprises at least one sealed cavity and each of the at least one sealed cavity is filled with one or more gases, and the transducer assembly comprises transducer elements configured to perform one or both of transmitting and receiving acoustic energy.

23 Claims, 9 Drawing Sheets

(56) References Cited

U.S. PATENT DOCUMENTS

| | | | |
|---|---|---|---|
| 2007/0167821 A1* | 7/2007 | Lee | A61B 8/12 600/463 |
| 2008/0097215 A1* | 4/2008 | Kliewer | A61B 8/4209 600/459 |
| 2008/0194961 A1* | 8/2008 | Randall | A61B 8/00 600/459 |
| 2009/0069689 A1* | 3/2009 | Isono | B06B 1/0629 600/459 |
| 2011/0077557 A1* | 3/2011 | Wing | A61B 8/546 601/2 |
| 2013/0172756 A1* | 7/2013 | Bruestle | A61B 8/4483 600/459 |
| 2015/0112201 A1* | 4/2015 | Nakanishi | A61B 8/4427 600/472 |
| 2016/0157819 A1* | 6/2016 | Song | A61B 8/4494 600/463 |
| 2018/0317883 A1* | 11/2018 | Huhtamaki | G10K 11/357 |

OTHER PUBLICATIONS

Hong, Zhou, et al. "Dielectric properties of polyimide/SiO2 hollow spheres composite films with ultralow dielectric constant." Materials Science and Engineering: B 203 (2016): 13-18. (Year: 2016).*
KR patent application 10-2020-0161228 filed Nov. 26, 2020—Office Action issued Nov. 8, 2022; English summary, 7 pages.

* cited by examiner

AIR FILLED CHAMBER IN AN ULTRASOUND PROBE

FIELD

Certain embodiments relate to an ultrasound probe. More specifically, certain embodiments relate to air filled chamber providing support in an ultrasound probe.

BACKGROUND

Medical imaging machines such as, for example, an ultrasound scanner, may be used for imaging at least a portion of a patient's body as part of diagnostic procedures. The ultrasound scanner may comprise a probe that emits, for example, sound waves.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

Air filled chamber(s) in an ultrasound probe, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in air filled chamber(s) in an ultrasound probe. The air filled chamber(s) (air chamber(s)) may also comprise structural support against external force when the ultrasound probe is pushed against, for example, a body part to form an image of a target.

The foregoing summary, as well as the following detailed description of certain embodiments will be better understood when read in conjunction with the appended drawings. The figures provided illustrate diagrams of the functional blocks of various embodiments, and the functional blocks are not necessarily indicative of the division between mechanical parts.

It should be understood that the various embodiments are not limited to the arrangements and instrumentality shown in the drawings, and that various embodiments may be combined. Other embodiments may be utilized and structural changes may be made without departing from the scope of the various embodiments. For example, different types of materials with similar mechanical properties may be used in various embodiments of the disclosure. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also, as used herein, the term "imaging machine" broadly refers to an ultrasound scanner. However, other devices and/or structures that need transmit and/or receive sound energy may also use an embodiment of the disclosure.

Figure 1:
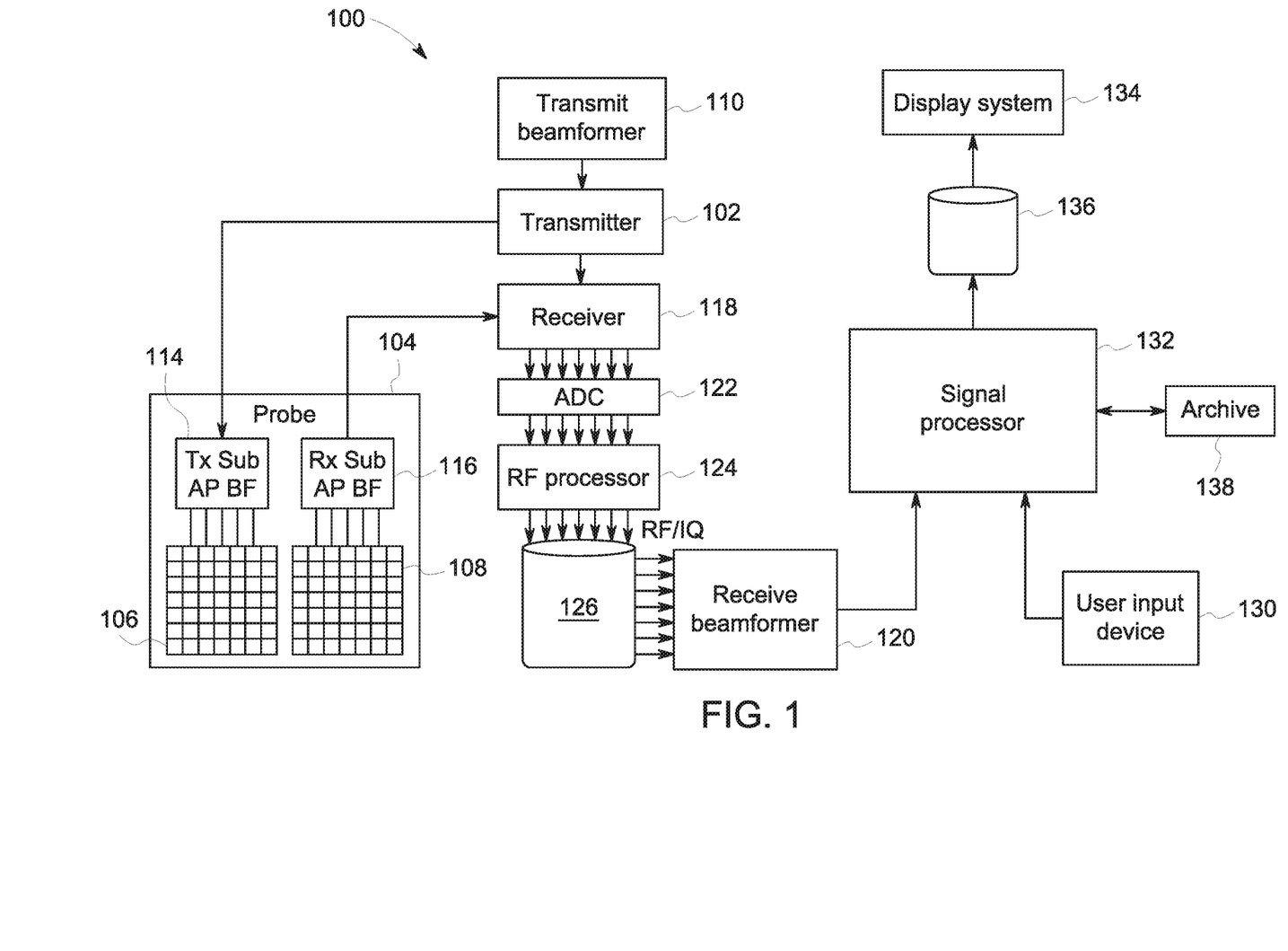
FIG. 1 is a block diagram of an exemplary ultrasound system, in accordance with various embodiments.

FIG. 1 is a block diagram of an exemplary ultrasound system 100, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mouse device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may be capable of receiving input information from a user input device 130 and/or archive 138, generating an output displayable by a display system 134, and manipulating the output in response to input information from a user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

Figure 2:
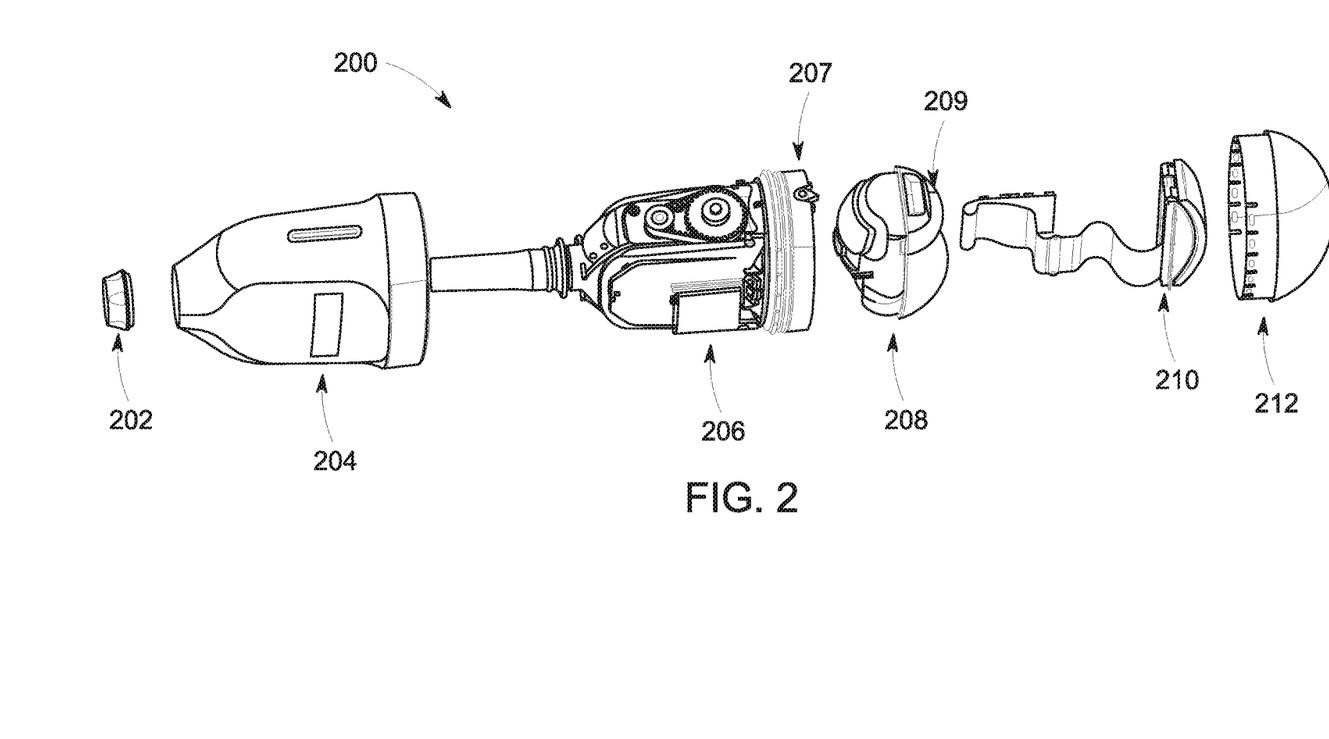
FIG. 2 is an exploded view of an exemplary probe for an ultrasound system, in accordance with various embodiments.

FIG. 2 is an exploded view of an exemplary probe for an ultrasound system, in accordance with various embodiments. Referring to FIG. 2, there is shown an exploded view of an ultrasound probe 200, where the ultrasound probe 200 may be similar in functionality to the ultrasound probe 104. As shown in FIG. 2, there is a nut 202, a handle 204, a receiving assembly 206, an air chamber unit 208, transducer assembly 210, and a transducer cap 212.

The receiving assembly 206 is inserted in the handle 204. It should be noted that while the nut 202 is depicted as coupling the receiving assembly 206 to the handle 204, various embodiments of the disclosure may use any of a number of different methods to couple the handle 204 to the receiving assembly 206. For example, the receiving assembly 206 may be snapped into the handle 204, the receiving assembly 206 may be coupled to the handle 204 with adhesive(s), the receiving assembly 206 may be screwed onto the handle 204, the receiving assembly 206 may be pressure fitted to the handle 204, etc.

An air chamber frame 207 in the receiving assembly 206 is configured to receive the air chamber unit 208. The air chamber unit 208 is configured to receive the transducer assembly 210 in the transducer slot 209, and the transducer cap 212 is configured to cover at least the transducer assembly 210. Accordingly, when assembled, the ultrasound probe 200 shows the handle 204 and the transducer cap 212, where a cable (not shown) may exit the handle 204. The cable may electrically connect the ultrasound probe 200 to provide power and to communicate signals to and from the ultrasound probe 200. The transducer assembly 210 may be swiveled to allow the transducer assembly 210 to transmit ultrasound waves at different directions and receive the echoed ultrasound waves from different directions. The transducer cap 212 may serve to protect the transducer assembly 210 from the environment external to the transducer assembly 210.

When the ultrasound probe 200 is pressed against, for example, a body part, various components of the ultrasound probe 200 may be under stress. For example, transducer assembly 210 may be forced against the air chamber unit 208. In order to prevent the air chamber unit 208 from deforming, the air chamber unit 208 may need to have structural strength to prevent deforming due to external forces. Deformation of the air chamber unit 208 may point the transducer assembly 210 in a direction that is not desired.

Accordingly, the air chamber unit 208, at least a portion of which comprises a sealed cavity filled with one or more gases such as, for example, air, may be designed to withstand an application force as well as impact and drop forces during handling or potential misuse of the product. The greatest forces may arise from drop of the product during use or transport. For example, regulatory standards may require the ultrasound probe 200 to be able to remain electrically safe after a drop of 1.22 meters on a tiled concrete floor.

Therefore, the air chamber unit 208 may be designed structurally to withstand a requisite amount of force. This may be done by using a certain type of material and a corresponding thickness of that material to withstand a predetermined force, or structural designs to withstand a predetermined force by dissipating force through various support structures. For example, at least a portion of the walls may be corrugated, there may be braces for at least a portion of the walls, there may be support(s) inside the sealed cavity, etc.

The air chamber unit 208 may comprise, for example, a plurality of molded parts that are bonded and sealed (joined together) using laser welding and/or ultrasound welding. The air chamber unit 208 may comprise, for example, a plurality of molded parts that are bonded and sealed (joined together) with one or more adhesives. The air chamber unit 208 may comprise, for example, a single part formed from foamed material, where the foamed material is molded or machined. The air chamber unit 208 may comprise, for example, a single part formed by an additive process of one or more material, which may include 3-dimensional printing. The air chamber unit 208 may comprise, for example, a single part formed by formed by gas injection molding. The air chamber unit 208 may comprise, for example, a single part formed by rotational molding.

While various examples are given for forming the air chamber unit 208, various embodiments of the disclosure need not be limited to these examples. Additionally, any part of the air chamber unit 208 may comprise multiple materials of different type, and different parts of the air chamber unit 208 may be formed by a different process and/or from different materials.

The directional control of the transducer assembly 210 may be provided by, for example, the RF processor 124, the signal processor 132, and/or the user input device 130 controlling a drive assembly of the ultrasound probe 200. For example, the drive assembly may comprise a stepper motor (not shown) in the ultrasound probe 200 that may rotate the transducer assembly 210 by means of a gear. However, various embodiments may use other processors/devices to control the direction of the transducer assembly 210.

Various parts of the ultrasound probe 200 may be coupled together. In some cases, the coupling may be removable coupling, while in other cases, the coupling may be permanent coupling. Removable coupling may allow, for example, two parts to be uncoupled from each other without functional damage to the parts so that the parts can be removably coupled together again. Permanent coupling may be, for example, when two parts cannot be uncoupled without performing functional damage to the parts. As an example, removable coupling may be with nuts and bolts, while permanent coupling may be by welding or with a very strong adhesive such that trying to separate two parts result in damage to one or both of the parts.

Figure 3:
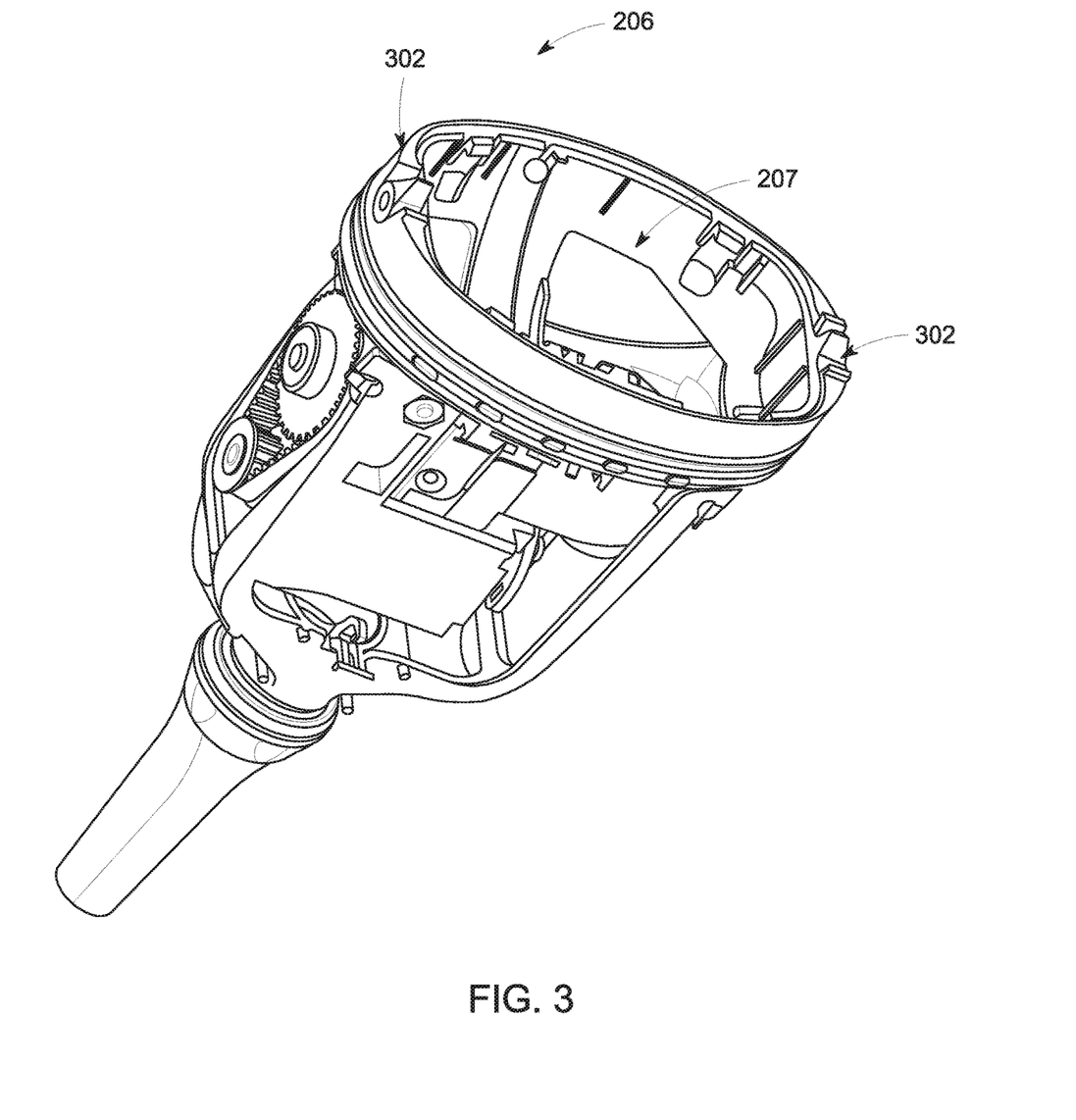
FIG. 3 is a receiving assembly for a transducer for the exemplary ultrasound probe, in accordance with various embodiments.

FIG. 3 is a receiving assembly for a transducer for the exemplary ultrasound probe, in accordance with various embodiments. Referring to FIG. 3, there is shown the receiving assembly 206 comprising the air chamber frame 207. The air chamber frame 207 may comprise coupling points 302. The air chamber unit 208 may be received by the air chamber frame 207 and supported by the coupling points 302 such that the air chamber unit 208 can swivel about, for example, an axis formed along the coupling points 302. It may be noted that while an embodiment of the disclosure describes a gas filled cavity, other embodiments may use a vacuum in the cavity, where the level of vacuum may vary. Alternatively, composite material such as, for example, a closed cell foam or composite material from hollow structures may be used to fill the cavity in entirety or in part. For example, the cavity may comprise composite material with gas filled glass micro bubbles. The composite material may also, for example, provide structural support.

Accordingly, an ultrasound probe 200 with the air chamber unit 208, whether provided with vacuum, filled with air, and/or composite material, may be reduced in weight compared to other probes that may use coupling fluid. The reduced weight for the ultrasound probe 200 provides for reduced momentum of the rotating parts, such as, for example, the transducer assembly 210, reduce turbulence of the fluid that may be used otherwise, reduce the fluid quantity and resistance to movement by the fluid, etc.

Additionally, a lighter ultrasound probe 200 may provide easier use by an operator that is wielding the ultrasound probe 200. There may also be better balance of the ultrasound probe 200 due to the reduced weight in the transducer assembly 210. Accordingly, the operator wielding the lighter ultrasound probe 200 may work in greater comfort as well as reducing chances of hand/wrist/arm injury.

Furthermore, reducing the weight of the ultrasound probe 200 also reduces the chances of damage if it is dropped or hit against another object.

Figure 4:
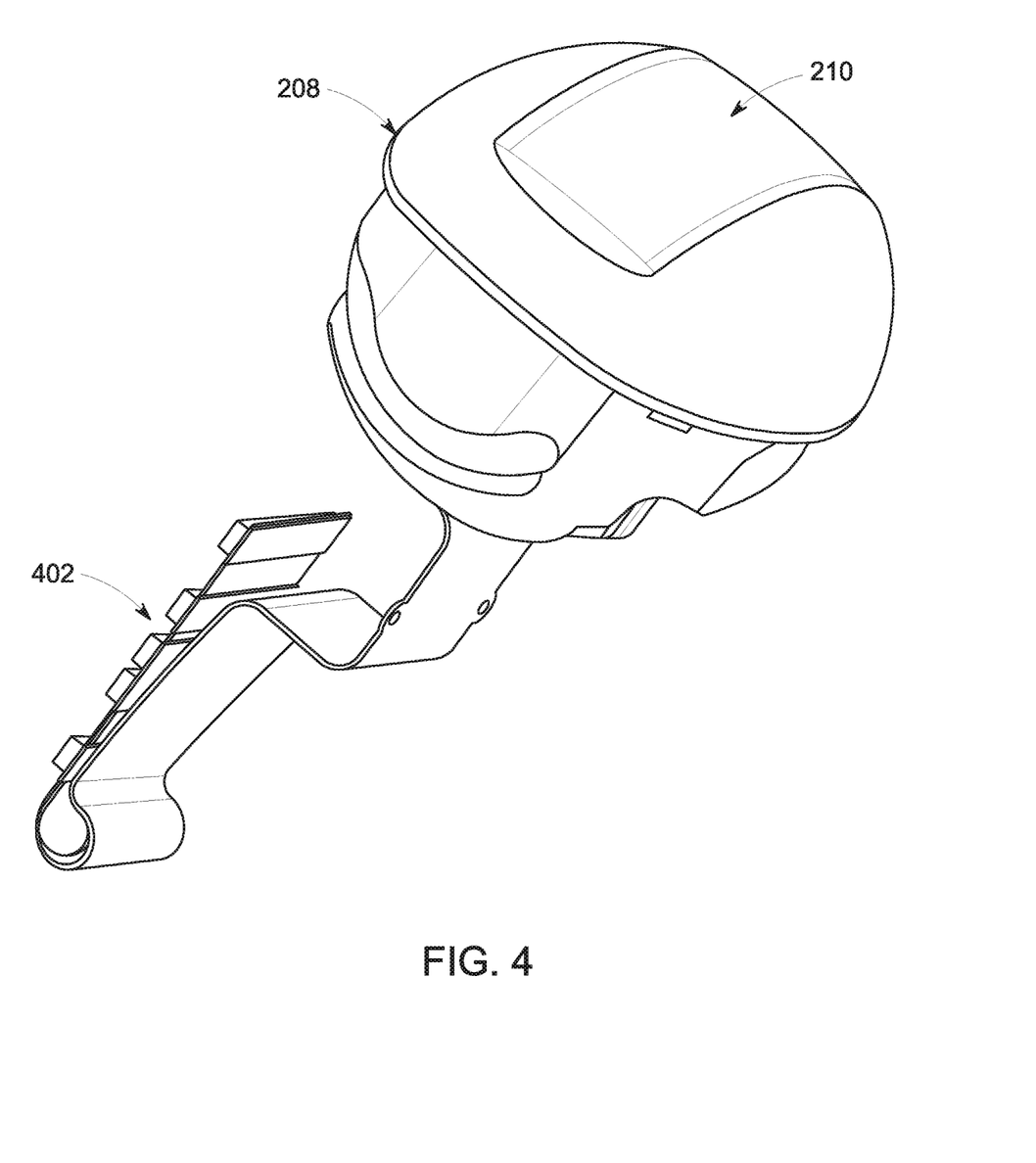
FIG. 4 is an illustration of an air chamber and the transducer for the exemplary ultrasound probe, in accordance with various embodiments.

FIG. 4 is an illustration of an air chamber and the transducer for the exemplary ultrasound probe, in accordance with various embodiments. Referring to FIG. 4, there is shown the air chamber unit 208 and the transducer assembly 210. The transducer assembly 210 fits into the transducer slot 209 of the air chamber unit 208. The electrical connections 402 from the transducer assembly 210 may, for example, go through an opening in the air chamber unit 208 to electrically connect to the receiving assembly 206.

Accordingly, electrical signals, as well as power and ground connections, may be communicated to and from the ultrasound probe 200 through a cable (not shown) to the handle 204. The cable may be connected to, for example, the receiving assembly 206 such that a processor such as, for example, the RF processor 124, the signal processor 132, or some other processor may be able to control movement of the transducer assembly 210. The RF processor 124, the signal processor 132, etc., may also control acoustic output of the transducer assembly 210, as well as receive received acoustic signals by the transducer assembly 210.

In some embodiments, the transducer assembly 210 may be removably coupled to the air chamber unit 208, while in other embodiments, the transducer assembly 210 may be permanently coupled to the air chamber unit 208.

Figure 5A:
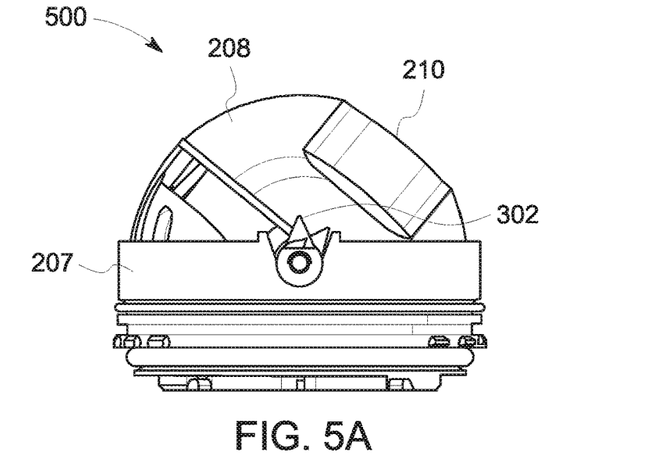
FIGS. 5A-5C illustrate motion of the transducer for the exemplary ultrasound probe, in accordance with various embodiments.
Figure 5B:
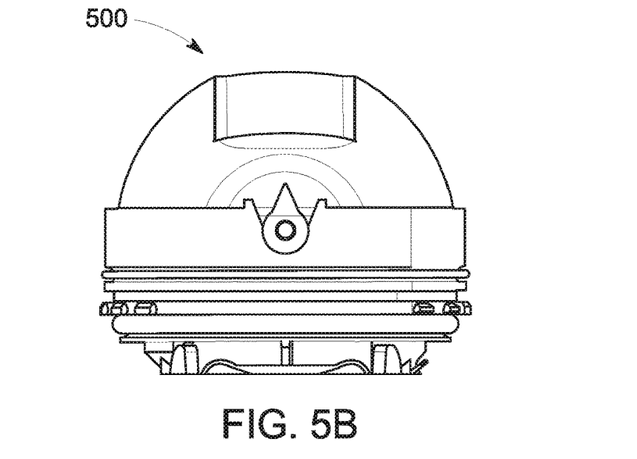
Figure 5C:
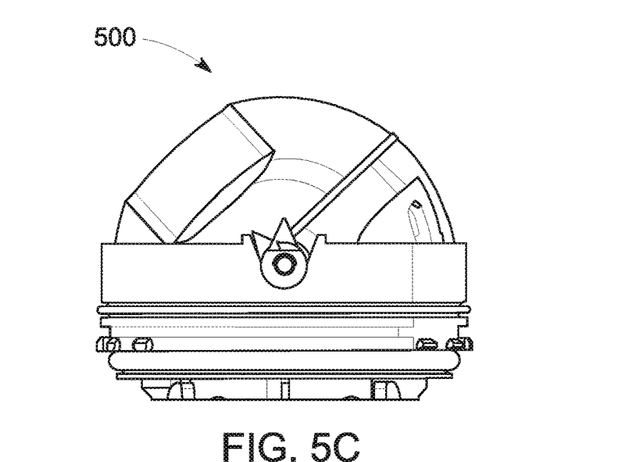

FIGS. 5A-5C illustrate motion of the transducer for the exemplary ultrasound probe, in accordance with various embodiments. FIGS. 5A-5C illustrate the transducer assembly 210 coupled to the air chamber unit 208, and the air chamber unit 208 coupled to the receiving assembly 206 via the air chamber frame 207. As can be seen, the coupled unit 500 can be controlled to swivel to different directions. For example, FIG. 5A shows the coupled unit 500 angled to the right, FIG. 5B shows the coupled unit 500 pointing straight up, and FIG. 5C shows the coupled unit 500 angled to the left.

Figure 6A:
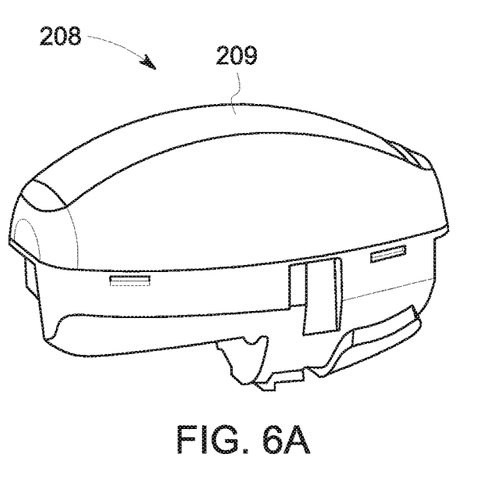
FIGS. 6A-6C illustrate a side cross-section view of an exemplary air chamber for the exemplary ultrasound probe, in accordance with various embodiments.
Figure 6B:
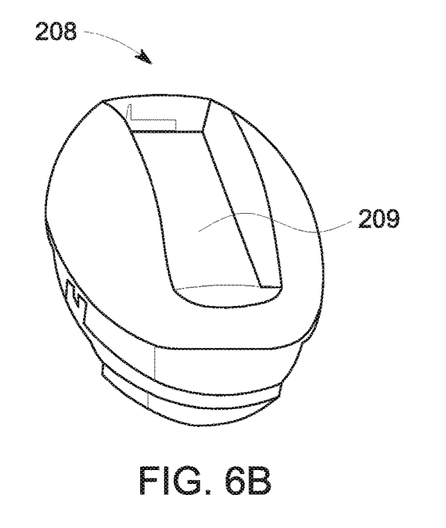
Figure 6C:
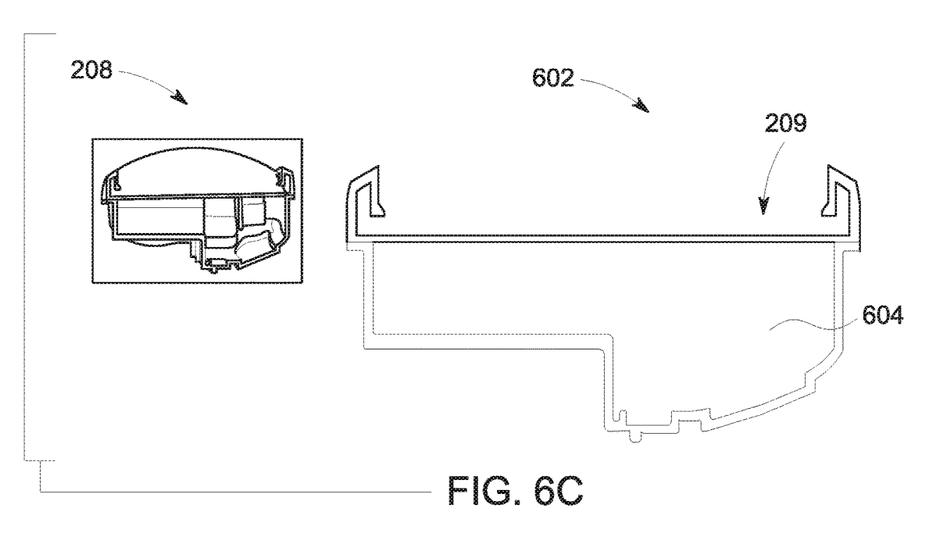

FIGS. 6A-6C illustrate a side cross-section view of an exemplary air chamber for the exemplary ultrasound probe, in accordance with various embodiments. Referring to FIGS. 6A and 6B, there are shown different views of the air chamber unit 208 with the transducer slot 209. In FIG. 6C, there is shown a side view of the air chamber unit 208, and a side cross-section view 602 of the air chamber unit 208. The transducer slot 209 is seen at the top of the side cross-section view 602, and an air cavity 604 is seen at the bottom portion of the side cross-section view 602.

Figure 7A:
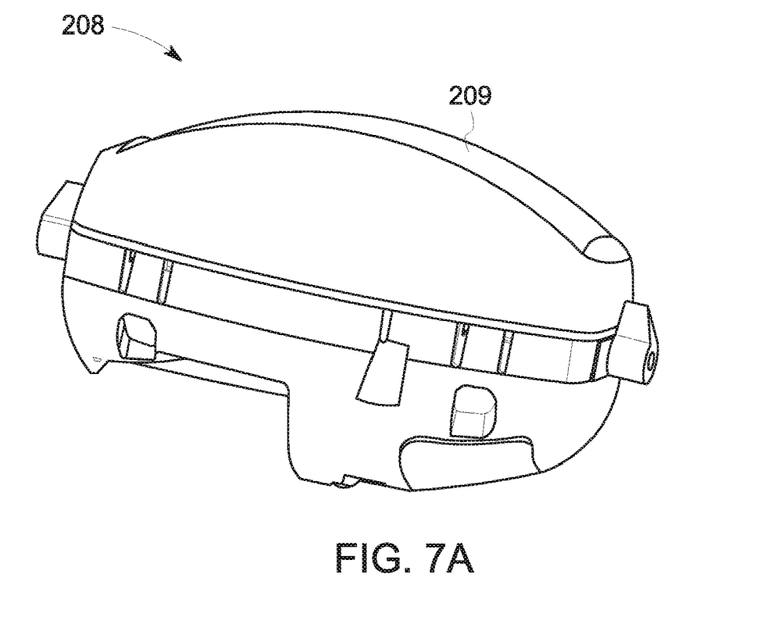
FIGS. 7A-7B illustrate a front cross-section view of the exemplary air chamber for the exemplary ultrasound probe, in accordance with various embodiments.
Figure 7B:
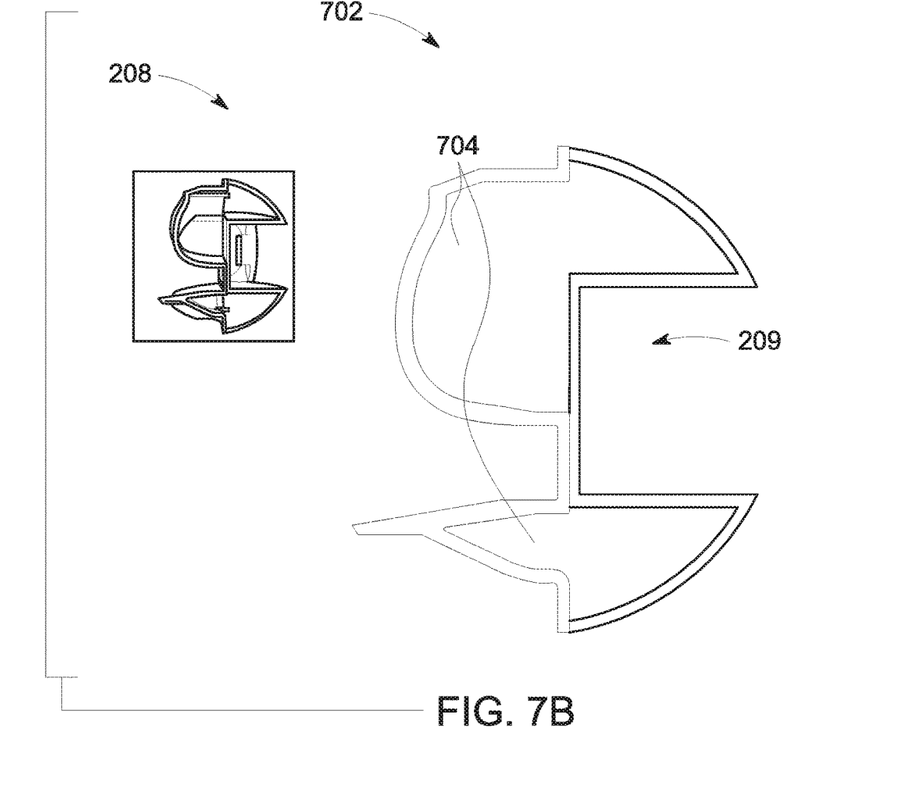

FIGS. 7A-7B illustrate a front cross-section view of the exemplary air chamber for the exemplary ultrasound probe, in accordance with various embodiments. Referring to FIG. 7A there is shown a substantially side view of the air chamber unit 208 with the transducer slot 209. In FIG. 7B, there is shown a front view of the air chamber unit 208, and a front cross-section view 702 of the air chamber unit 208. The transducer slot 209 is seen at the right side of the front cross-section view 702, and air cavities 704 are seen at the left portion of the front cross-section view 702.

Figure 8:
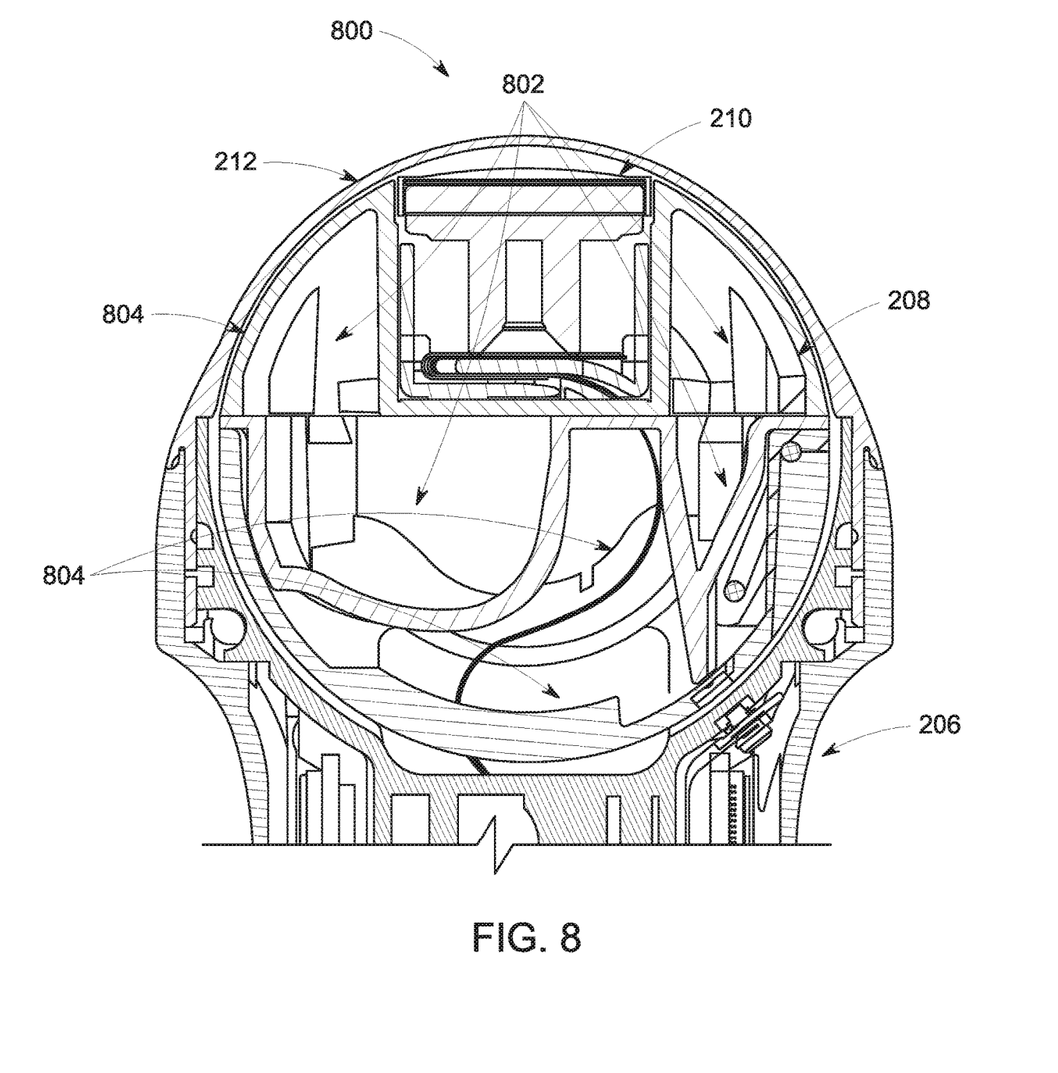
FIG. 8 illustrates a front cross-section view of an upper portion of the exemplary ultrasound probe, in accordance with various embodiments.

FIG. 8 illustrates a front cross-section view of an upper portion of the exemplary ultrasound probe, in accordance with various embodiments. Referring to FIG. 8, there is shown a cross-section view of a head portion 800 of the transducer probe 200 comprising the receiving assembly 206, the air chamber unit 208, the transducer assembly 210, and the transducer cap 212. There are also shown the air cavities 802 and fluids such as, for example, oil, in sections 804 of the air chamber unit 208.

Figure 9:
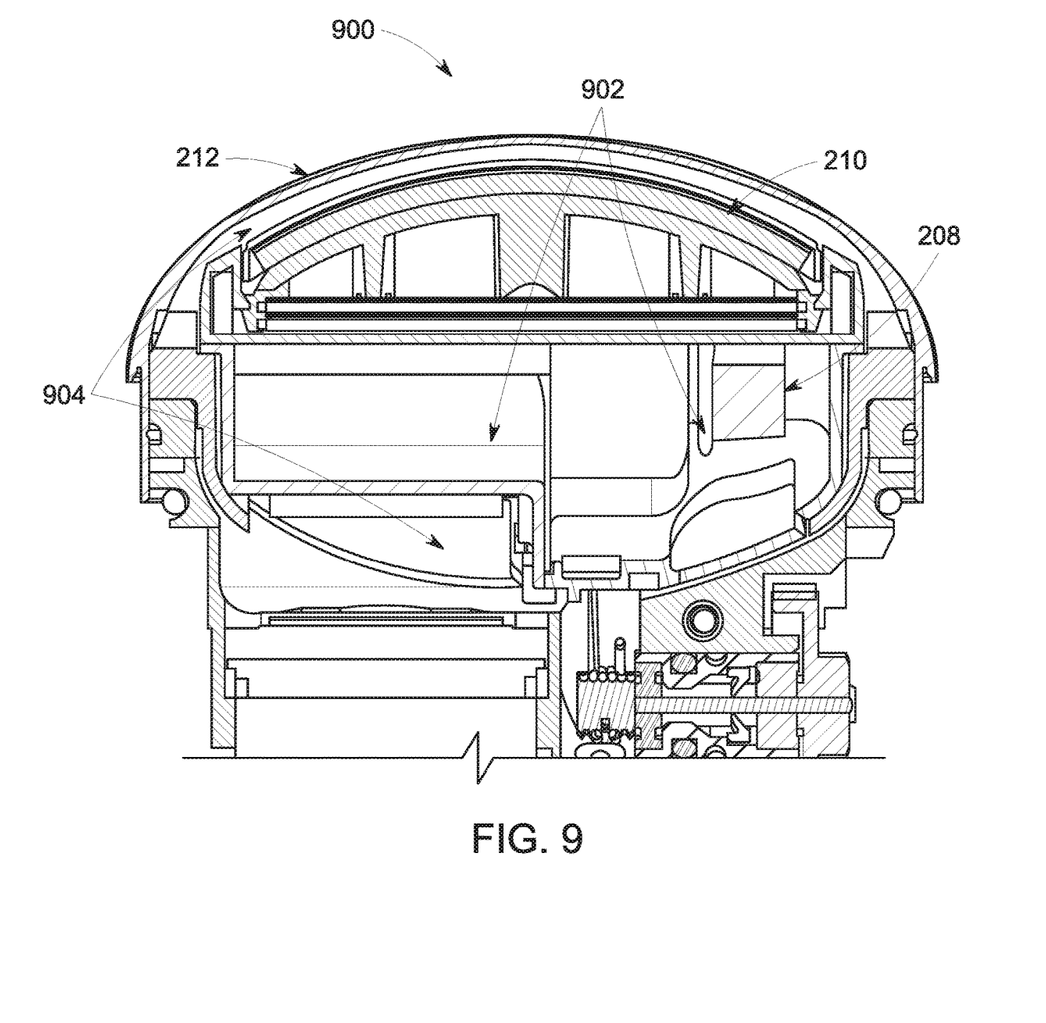
FIG. 9 illustrates a side cross-section view of an upper portion of the exemplary ultrasound probe, in accordance with various embodiments.

FIG. 9 illustrates a side cross-section view of an upper portion of the exemplary ultrasound probe, in accordance with various embodiments. Referring to FIG. 9, there is shown a cross-section view of a head portion 900 of the transducer probe 200 comprising the receiving assembly 206, the air chamber unit 208, the transducer assembly 210, and the transducer cap 212. There are also shown the air cavities 902 and fluids such as, for example, oil, in sections 904 of the air chamber unit 208.

While specific structures were shown regarding air filled cavities in FIGS. 6A-9, it should be understood that different embodiment of the disclosure may have different configurations for number/placement/shape of air cavity/cavities.

Accordingly, it can be seen that the disclosure provides for an ultrasound probe 200 that comprises an air chamber unit with 208 a transducer slot 209, where the transducer slot 209 is configured to receive a transducer assembly 210. The air chamber unit 208 may comprise at least one sealed cavity 802/902, each of the at least one sealed cavity 802/902 may be filled with one or more gases, where the gas may be, for example, air. The transducer assembly 210 may comprise transducer elements 106/108 configured to perform one or both of transmitting and receiving acoustic energy.

The ultrasound probe 200 may comprise a receiving assembly 206 with an air chamber frame 207 configured to receive the air chamber unit 208 into the air chamber frame 207. The ultrasound probe 200 may comprise a handle 204 configured to receive the receiving assembly 206 into the handle 204. The receiving assembly 206 may be configured to be coupled to the handle 204 using any of a number of appropriate methods such as, for example, a nut 202, adhesives, snapping the receiving assembly 206 into the handle 204, screwing the receiving assembly 206 to the handle 204, pressure fitting the receiving assembly 206 to the handle 204, etc.

The ultrasound probe 200, when the transducer assembly 210 is received by the air chamber unit 208 in the transducer slot 209, the transducer assembly 210 and the air chamber unit 208 may be configured to swivel together. The ultrasound probe 200 may comprise a transducer cap 212 configured to be fixed to the receiving assembly 206 and/or a handle 204 configured to receive the receiving assembly 206.

The air chamber unit 208 for the ultrasound probe 200 may comprise, for example, molded parts bonded and sealed using one or both of laser and ultrasound welding. The air chamber unit 208 may comprise, for example, molded parts bonded and sealed with one or more adhesives. The air chamber unit 208 may comprise, for example, a single part formed from foamed material, where the foamed material is molded or machined. The air chamber unit 208 may comprise, for example, a single part formed by additive process. The air chamber unit 208 may comprise, for example, a single part formed by gas injection molding. The air chamber unit 208 may comprise, for example, a single part formed by rotational molding.

The disclosure also provides for an ultrasound probe 200 that comprises an air chamber unit 208 comprising a transducer slot 209, where the transducer slot 209 is configured to receive a transducer assembly 210. The air chamber unit 208 may comprise at least one sealed cavity 802/902, where each of the at least one sealed cavity 802/902 may be filled at least in part with composite material, and the transducer assembly 210 may comprise transducer elements 106/108 configured to perform one or both of transmitting and receiving acoustic energy. The composite material may comprise, for example, hollow structures with gas filled glass micro bubbles and/or closed cell foam.

The disclosure further provides for an ultrasound probe that comprises a handle 204 configured to receive a receiving assembly 206, an air chamber unit 208 configured to be received by an air chamber frame 207 of the receiving assembly 206. A transducer assembly 210 may be configured to be received by the air chamber unit 208, and a transducer cap 212 may be configured to be placed over the transducer assembly 210.

The air chamber unit 208 may comprise a transducer slot 209 configured to receive the transducer assembly 210. The air chamber unit 208 may comprise at least one sealed cavity 802/902, where each of the at least one sealed cavity 802/902 may be filled with one or more gases, such as, for example, air. The transducer assembly 210 may comprise transducer elements 106/108 configured to perform one or both of transmitting and receiving acoustic energy.

The receiving assembly 206 may be configured to be coupled to the handle 204 using any of a number of appropriate methods such as, for example, a nut 202, adhesive(s), snapping the receiving assembly 206 into the handle 204, screwing the receiving assembly 206 to the handle 204, pressure fitting the receiving assembly 206 to the handle 204, etc. The transducer assembly 210 may be received by the air chamber unit 208 in the transducer slot 209, such that the transducer assembly 210 and the air chamber unit 208 may be configured to swivel together.

The transducer cap 212 may be configured to be fixed to the receiving assembly 206 and/or the handle 204. The air chamber unit 208 may comprise molded parts, and two or more of the molded parts may be bonded and sealed to each other with laser welding, ultrasound welding, and/or one or more adhesives.

The air chamber unit 208 may comprise a single part formed by foamed material that is molded or machined, additive process, gas injection molding, or rotational molding.

As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations.

Accordingly, the present disclosure may be realized with various materials. While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. An ultrasound probe, comprising:
a rigid air chamber unit comprising at least one sealed cavity, each of the at least one sealed cavity is filled with one or more gases;
a transducer assembly comprising transducer elements, the transducer elements configured to perform one or both of transmitting and receiving acoustic energy, the transducer assembly positioned adjacent an outer surface of the rigid air chamber unit, wherein the transducer assembly is separate and distinct from the rigid air chamber unit; and
a receiving assembly configured to receive the rigid air chamber unit, wherein the transducer assembly and the rigid air chamber unit are configured to swivel together with respect to the receiving assembly.

2. The ultrasound probe of claim 1, wherein the receiving assembly comprises an air chamber frame configured to receive the rigid air chamber unit into the air chamber frame.

3. The ultrasound probe of claim 1, comprising an electrical connection electrically connecting the transducer assembly to the receiving assembly.

4. The ultrasound probe of claim 2, comprising a transducer cap configured to be coupled to one or both of the receiving assembly and a handle configured to receive the receiving assembly.

5. The ultrasound probe of claim 1, wherein the rigid air chamber unit comprises molded parts bonded and sealed using one or both of laser and ultrasound welding.

6. The ultrasound probe of claim 1, wherein the rigid air chamber unit comprises molded parts bonded and sealed with one or more adhesives.

7. The ultrasound probe of claim 1, wherein the rigid air chamber unit comprises a single part formed from foamed material, wherein the foamed material is molded or machined.

8. The ultrasound probe of claim 1, wherein the rigid air chamber unit comprises a single part formed by additive process.

9. The ultrasound probe of claim 1, wherein the rigid air chamber unit comprises a single part formed by gas injection molding.

10. The ultrasound probe of claim 1, wherein the rigid air chamber unit comprises a single part formed by rotational molding.

11. The ultrasound probe of claim 1, wherein the one or more gases is air.

12. An ultrasound probe, comprising:
a non-deformable air chamber unit comprising at least one sealed cavity, each of the at least one sealed cavity is filled at least in part with composite material;
a transducer assembly comprising transducer elements, the transducer elements configured to perform one or both of transmitting and receiving acoustic energy, the transducer assembly seated against an outer surface of the non-deformable air chamber unit, wherein the transducer assembly is separate and distinct from the non-deformable air chamber unit; and
a receiving assembly configured to receive the non-deformable air chamber unit, wherein the transducer assembly and the non-deformable air chamber unit are configured to swivel together with respect to the receiving assembly.

13. The ultrasound probe of claim 12, wherein the composite material comprises hollow structures with gas filled glass micro bubbles.

14. The ultrasound probe of claim 12, wherein the composite material comprises closed cell foam.

15. An ultrasound probe, comprising:
a handle configured to receive a receiving assembly;
a rigid air chamber unit configured to be received by an air chamber frame of the receiving assembly, the rigid air chamber unit comprising at least one sealed cavity, each of the at least one sealed cavity filled with one or more gases;
a transducer assembly comprising transducer elements, the transducer elements configured to perform one or both of transmitting and receiving acoustic energy, the transducer assembly configured to abut an outer surface of the rigid air chamber unit, wherein the transducer assembly is separate and distinct from the rigid air chamber unit; and a transducer cap configured to be placed over the transducer assembly, wherein when the transducer assembly abuts the outer surface of the rigid air chamber unit, the transducer assembly and the rigid air chamber unit are configured to swivel together with respect to the receiving assembly.

16. The ultrasound probe of claim 15, comprising an electrical connection electrically connecting the transducer assembly to the receiving assembly.

17. The ultrasound probe of claim 15, wherein the transducer cap is configured to be coupled to one or both of the receiving assembly and the handle.

18. The ultrasound probe of claim 15, wherein the one or more gases is air.

19. The ultrasound probe of claim 15, wherein the rigid air chamber unit comprises molded parts, and two or more of the molded parts are bonded and sealed to each other with one or more of:
    laser welding;
    ultrasound welding; and
    one or more adhesives.

20. The ultrasound probe of claim 15, wherein the rigid air chamber unit comprises a single part formed by one of:
    foamed material that is molded or machined;
    additive process;
    gas injection molding; or
    rotational molding.

21. The ultrasound probe of claim 15, wherein:
    the outer surface of the rigid air chamber unit comprises an indentation, and the transducer assembly having the transducer elements is configured to abut the outer surface of the rigid air chamber unit in the indentation.

22. The ultrasound probe of claim 1, wherein:
    the outer surface of the rigid air chamber unit comprises a groove, and
    the transducer assembly having the transducer elements is configured to be positioned against the groove in the outer surface of the rigid air chamber unit.

23. The ultrasound probe of claim 12, wherein:
    the outer surface of the non-deformable air chamber unit comprises a depression, and
    the transducer assembly having the transducer elements is configured to be seated within the depression in the outer surface of the non-deformable air chamber unit.

* * * * *